United States Patent
Van Steenwinckel et al.

(10) Patent No.: US 9,534,250 B2
(45) Date of Patent: Jan. 3, 2017

(54) SENSING DEVICE AND MANUFACTURING METHOD THEREOF

(75) Inventors: David Van Steenwinckel, Holsbeek (BE); Filip Frederix, Tervuursesteenweg (BE)

(73) Assignee: NXP B.V., Eindhoven (NL)

( * ) Notice: Subject to any disclaimer, the term of this patent is extended or adjusted under 35 U.S.C. 154(b) by 1514 days.

(21) Appl. No.: 13/095,790

(22) Filed: Apr. 27, 2011

(65) Prior Publication Data

US 2011/0269646 A1    Nov. 3, 2011

(30) Foreign Application Priority Data

Apr. 30, 2010 (EP) .................................. 10161670

(51) Int. Cl.
*C12Q 1/68* (2006.01)
*C40B 50/18* (2006.01)
*C40B 60/12* (2006.01)
*C40B 50/14* (2006.01)

(52) U.S. Cl.
CPC ............. *C12Q 1/6837* (2013.01); *C40B 50/18* (2013.01); *C40B 60/12* (2013.01); *B01J 2219/00529* (2013.01); *B01J 2219/00576* (2013.01); *B01J 2219/00608* (2013.01); *B01J 2219/00653* (2013.01); *B01J 2219/00722* (2013.01); *C40B 50/14* (2013.01)

(58) Field of Classification Search
CPC ................... C12Q 1/6837; B01J 2219/00529; B01J 2219/00576; B01J 2219/00608; B01J 2219/00653; B01J 2219/00722; C40B 50/14; C40B 50/18; C40B 60/12
See application file for complete search history.

(56) References Cited

U.S. PATENT DOCUMENTS

| | | | |
|---|---|---|---|
| 6,632,655 B1 | 10/2003 | Mehta et al. | |
| 7,303,875 B1 * | 12/2007 | Bock et al. | .............. 435/6.11 |
| 2002/0064775 A1 | 5/2002 | Choong et al. | |
| 2005/0130173 A1 | 6/2005 | Leamon et al. | |
| 2005/0153290 A1 * | 7/2005 | Van Beuningen | ....... C12Q 1/68 |
| | | | 435/6.11 |
| 2009/0153130 A1 | 6/2009 | Shim et al. | |

FOREIGN PATENT DOCUMENTS

| | | |
|---|---|---|
| WO | 2007/030484 A2 | 3/2007 |
| WO | 2009/060379 A2 | 5/2009 |
| WO | 2009/074926 A1 | 6/2009 |

OTHER PUBLICATIONS

Strohsahl et al. (Talanta, 2005, 67:479-485).*
Schena et al. (Science, 1995, 20:467-470).*
Kerman et al. (Meas. Sci. Technol., 2004, 15:R1-R11).*
Koehne et al. (Clinical Chemistry, 2004, 50:1886-1893).*

(Continued)

*Primary Examiner* — Jeremy C Flinders

(57) ABSTRACT

The present invention relates to a sensing device with a surface having at least one individual sensing region, wherein each sensing region includes a plurality of binding elements anchored on the surface for binding different specific analytes of interest, at least one of the analyte of interest and its matching binding element having a label for detecting said binding. The present invention further relates to a method of manufacturing such a sensing device.

20 Claims, 2 Drawing Sheets

(56) References Cited

OTHER PUBLICATIONS

Brinkers, S. et al. "The Persistence Length of Double Stranded DNA Determined Using Dark Field Tethered Particle Motion", J. of Chemical Physics, vol. 130, pp. 215105-1-215105-9 (2009).

Vollmer, F. et al "Multiplexed DNA Quantification by Spectroscopic Shift of Two Microsphere Cavities", Biophysical J., vol. 85, pp. 1974-1979 (Sep. 2003).

Vollmer, F. "Taking Detection to the Limit Label-Free, High Sensitivity Detection of Biomolecules Using Optical Resonance", B.I.F. FUTURA, vol. 20, pp. 239-244 (2005).

Vollmer, F. et al "Whispering-Gallery-Mode Biosensing: Label-Free Detection Down to Single Molecules", Nature Methods, vol. 5, No. 7, pp. 591-596, (Jul. 2008).

Dietrich, H. et al. "Tethered Particle Motion Mediated by Scattering from Gold Nanoparticles and Darkfield Microscopy", J. of Nanophotonics, vol. 3, 031795, 17 pgs. (Jun. 22, 2009).

Extended European Search Report for European Patent Appln. No. 10161670.4 (Sep. 10, 2010).

\* cited by examiner

SENSING DEVICE AND MANUFACTURING METHOD THEREOF

This application claims the priority under 35 U.S.C. §119 of European patent application no. 10161670.4, filed on Apr. 30, 2010, the contents of which are incorporated by reference herein.

FIELD OF THE INVENTION

The present invention relates to a sensing device comprising a surface having a plurality of individual sensing regions.

The present invention further relates to a method of manufacturing such a sensing device.

BACKGROUND OF THE INVENTION

Single molecule detection has become a reality in application domains such as healthcare. For instance, the use of techniques such as tethered particle motion (TPM) has made it possible to detect the binding of a single biomolecule, from hereon referred to as the analyte of interest, to a receptor anchored on the surface of a sensing device. The binding event typically alters the molecular dynamics of the receptor, which can be detected using optical or electrical detection techniques.

For instance, in case of the receptor comprising a nucleotide sequence such as a DNA fragment, prior to a binding event with a complementary nucleotide sequence the receptor may adopt a coiled-up or U-shaped (looped) conformation, e.g. due to the presence of a (partial) palindrome in the nucleotide sequence, with the conformation becoming more stretched or linear when a binding event takes place. This change in conformation affects, i.e. increases the volume of Brownian motion that the receptor inhabits. This change in volume may be detected by attaching a label to the receptor or the analyte of interest and recording the motion of the label.

Several examples of recording the trajectory of such a label, i.e. a metal nanoparticle or bead, are disclosed in a paper by H. R. C. Dietrich et al. in Journal of Nanophotonics, Vol. 3 (2009), pages 1-17. These detection techniques are based on an optical detection of the motion of the particle, including darkfield microscopy and the whispering gallery mode detection method, the latter method being particularly suitable for integration in semiconductor devices such as integrated circuits (ICs).

It is also possible to detect such changes electrically, as the aforementioned conformation change alters the effective dielectric constant directly above the surface of the sensing device. This effect may be utilized by defining the volume directly above the surface of the sensing device in which the receptor resides as the dielectric layer of a capacitor, such that the changes in dielectric constant are translated in a change in capacitance of the capacitor. In addition, when using metal beads as labels, the distance of the bead to the sensing surface is also correlated to the effective potential of the sensing surface, which, for instance when using the surface as the gate electrode of a transistor formed in the substrate of the sensing device, can be used to influence the conductivity of the transistor. Other suitable detection techniques are known to the skilled person.

It is particularly attractive to have a sensing device that is capable of implementing a high degree of multiplexing, such that the device can detect a large number of different analytes of interest in a single measurement procedure. An example of such a device is given in WO 2009/060379 A2, which utilizes the whispering gallery mode detection method for detecting a binding event. Particular attention is drawn to FIG. 6 and its detailed description in which the whispering gallery mode detection method is explained in detail. The sensing device disclosed in this patent application comprises a plurality of sensor active structures that are each functionalized with a different biomolecule such that the sensing device is capable of detecting a different analyte of interest at each sensor active region.

It is desirable to increase the degree of multiplexing to the highest possible extent, as a higher degree of multiplexing allows for more analytes of interest to be simultaneously detected. Currently, a sensing region is functionalized with its receptor, e.g. a biomolecule for binding to an analyte of interest by depositing the biomolecule onto the sensor region dissolved in a droplet of liquid. The dimensions of the droplet thus govern how many sensor regions may be defined onto a surface of a sensing device such an IC comprising a sensing surface. Currently, advanced deposition tools allow for the deposition of droplets having a 5 μm diameter at a 10 μm distance from each other. As the size of an IC ideally is kept as small as possible, e.g. for cost reasons, it will be appreciated that it is far from trivial to produce a sensing device in a cost-effective manner that allows for a high level of multiplexing.

SUMMARY OF THE INVENTION

The present invention seeks to provide a sensing device comprising a surface having a plurality of individual sensing regions allowing for an increased degree of multiplexing.

The present invention further seeks to provide a method for manufacturing such a sensing device.

In accordance with an aspect of the present invention, there is provided a sensing device comprising a surface having at least one individual sensing region, wherein each sensing region comprises a plurality of binding elements anchored on said surface for binding different specific analytes of interest, at least one of the analyte of interest and its matching binding element comprising a label for detecting said binding.

The present invention has been based on the insight that the resolution of well-known detection techniques for single molecule detection, e.g. TPM detection techniques is such that at a sensing surface having an area at least the size of a single droplet, multiple binding events can be individually detected, as long as these binding events have a different detection signature. Hence, by providing a single sensing surface with multiple binding elements that exhibit different molecular dynamical behavior, the multiplicity of the sensing device is increased by a factor N, with N being the integer number of binding elements that are anchored on each sensing region compared to a sensing device having the same number of sensing regions but only a single binding element per sensing region.

Preferably, each binding element is unique, i.e. a particular binding element occurs on a single sensing region only, as this maximizes the degree of multiplexing of the sensing device.

In an embodiment, the binding elements on each sensing region comprise biological molecules having different chain lengths. Consequently, the biological molecules, when engaging in their respective binding events will generate sufficiently different detection signals to allow for the detection of the individual binding events.

Alternatively, the biological molecules are anchored on a sensing region surface by respective spacer molecules having different lengths.

Particularly suitable are biological molecules that comprise a nucleotide chain, such as RNA and DNA strands.

In an embodiment, the label comprises a bead. Suitable materials for the beads include magnetic materials, metals such as gold, polymer materials such as polystyrene and so on. In particular, when using an optical detection method, a bead may be used that has favorable characteristics for scattering incident electromagnetic radiation such as light.

In an embodiment, the sensing device further comprises detection means for detecting the binding of a specific analyte of interest to its matching binding element. For instance, when the sensing device comprises an integrated circuit, said sensing regions may be arranged on a surface of said integrated circuit, and the detection means may form part of the integrated circuit and comprise a plurality of circuit elements respectively coupled to the sensing regions for electrically detecting the binding of a specific analyte of interest to its matching binding element. Alternatively, the detection means may comprise optical means for optically detecting the binding of a specific analyte of interest to its matching binding element.

The sensing device of the present invention may be included in an apparatus further comprising output means for providing a sensing result to a user of said apparatus, e.g. a loud speaker, display device or other optical means for indicating a measurement result to a user. Such an apparatus may for instance be used by untrained users, e.g. patients, for self-diagnosis. Alternatively, the apparatus may be used by healthcare professionals in a diagnostic setup, e.g. infectious disease testing, life science affinity testing, veterinary diagnostics and so on.

In accordance with another aspect of the present invention, there is provided a method of manufacturing a sensing device comprising a surface having a plurality of individual sensing regions, the method comprising repeating, for each sensing region, the steps of providing a droplet on said sensing region, said droplet comprising a plurality of binding elements for binding different specific analytes of interest; and anchoring said binding elements on the surface of said sensing region. The provision of a droplet of a solution comprising a plurality of different binding elements such as biological molecules having a different chain length, e.g. nucleotide sequences of different lengths, or biological molecules anchored to said surface using different length spacer molecules, allows for the functionalization of a single sensing region with at least two different binding elements, thereby increasing the degree of multiplexing of the sensing device.

Preferably, each binding element comprises a label for detecting the binding of the corresponding specific analyte of interest to said binding element.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
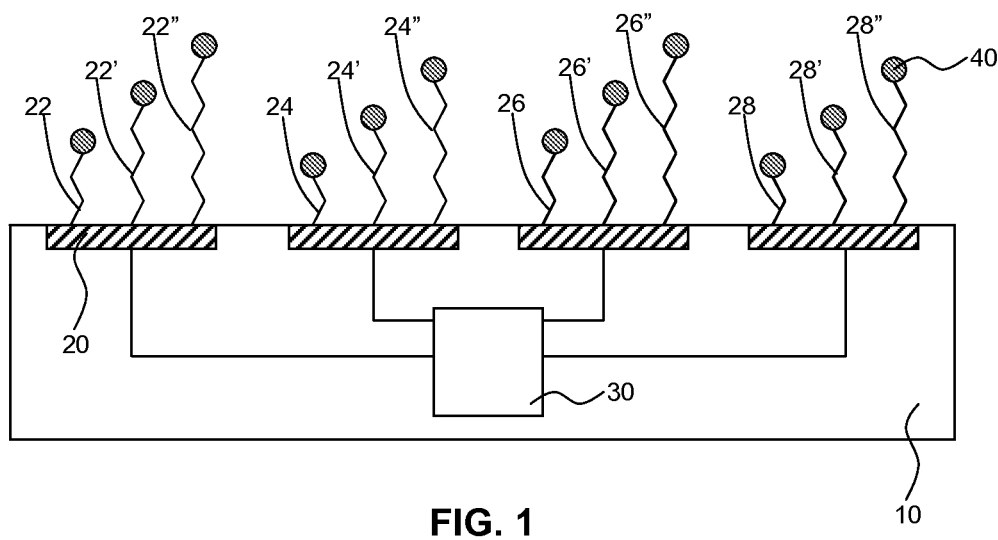
FIG. 1 schematically depicts a cross-section of a sensing device in accordance with an embodiment of the present invention.

It should be understood that the Figures are merely schematic and are not drawn to scale. It should also be understood that the same reference numerals are used throughout the Figures to indicate the same or similar parts.

FIG. 1 shows an embodiment of the sensing device of the present invention in the form of an IC. The sensing device comprises a substrate 10, which may be any suitable substrate such as a silicon substrate, a silicon-on-insulator substrate, a Si/Ge substrate and so on, which carries at least one, and preferably a plurality of sensing regions 20 on its surface. Each of the sensing regions comprises a plurality, i.e. at least two, different biomolecules for binding a specific analyte of interest to the sensing region. In FIG. 1, four sensing regions 20 are shown, each comprising unique biomolecules, i.e. biomolecules 22, 22' and 22" on a first sensing region 20, biomolecules 24, 24' and 24" on a second sensing region 20, biomolecules 26, 26' and 26" on a third sensing region 20 and biomolecules 28, 28' and 28" on a fourth sensing region 20. Any suitable types of biomolecules may be used, e.g. RNA or DNA strands, antibodies, antibody fragments, proteins and so on.

It is noted that it is preferred that the biomolecules at the various sensing surfaces 20 are unique, i.e. occur only once in the sensing device such that the degree of multiplexing provided by the sensing regions 20 is maximized. This is however not a prerequisite of the present invention. It is for instance equally feasible that the same biomolecule occurs at more than one sensing region 20, which for instance may be advantageous if the signal-to-noise ratio of the signal variation induced by a binding event single site is insufficient to reliably detect the binding event. The signal-to-noise ratio may be improved by the combination of the signals of the multiple sensing regions 20 carrying the same biomolecule.

It should be appreciated that each sensing region 20 comprises three different biomolecules by way of non-limiting example only. Each sensing region 20 may contain any suitable number of different biomolecules, and it is not necessary that each sensing region 20 contains the same number of biomolecules. In addition, it should be appreciated that the sensing device of the present invention may contain any suitable number of sensing regions 20.

Figure 2:
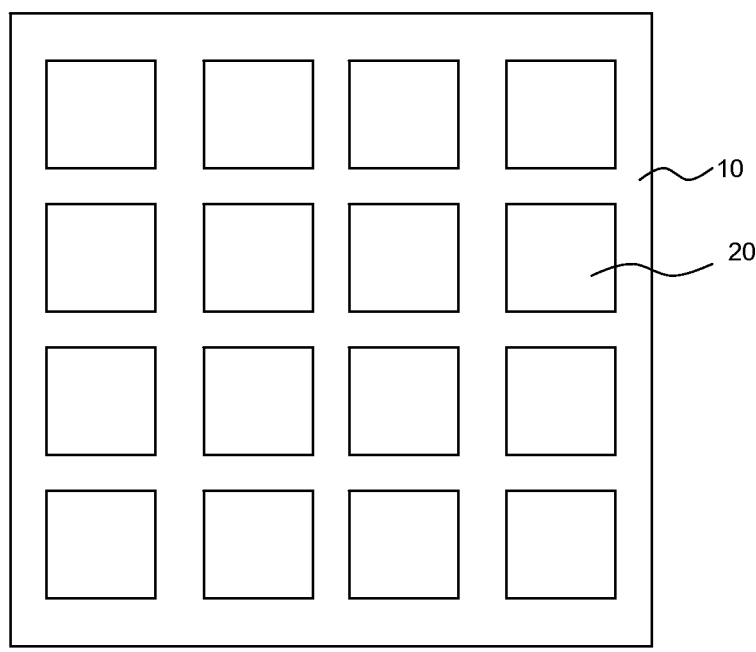
FIG. 2 schematically depicts a top view of the sensing device of FIG. 1.

In an embodiment, the sensing regions 20 may be arranged in a grid, as shown in FIG. 2, such that the sensing device has a tile-like pattern of sensing regions 20. The sensing regions 20 are shown as square tiles by way of non-limiting example only. Any suitable shape, e.g. rectangular, circular, and so on, may be chosen.

Upon returning to FIG. 1, the sensing device may further comprise detection means 30 for detecting an individual binding event on the respective sensing regions 20. For instance, when detecting a change in the dielectric constant of a volume directly above the sensing region 20, the detection means 30 may comprise a signal processing circuit for detecting a variation in a signal generated by the sensing region 20 at which the binding event has taken place.

Alternatively, the sensing device may comprise a generator (not shown) for generating electromagnetic radiation, e.g. one or more laser diodes, with the detection means 30 comprising one or more detectors, e.g. a CCD detector or a CMOS photodiode, for detecting electromagnetic radiation scattered by the beads 40 attached to the binding elements anchored at the surface of the respective sensing regions 20. The beads 40 preferably have the same size as this ensures that observed temporal variations in a scattering signal are predominantly caused by the tethered motion of the bead induced by the movements of the biomolecule to which the bead is attached.

In an embodiment, the biomolecules 22, 22', 22", 24, 24', 24", 26, 26', 26", 28, 28' and 28" may comprise biological strands having different chain lengths at each sensing region 20. Alternatively, similar or equal length biomolecules may be used with the required length differential introduced by different length spacer molecules, e.g. synthetic spacer molecules, anchoring the biomolecules to the sensing region 20. Each sensing region 20 may be functionalized with its plurality of biomolecules as follows. A mixture of the biomolecules dissolved or suspended in a liquid may be deposited by spotting on the intended sensor region 20. Spotting may be achieved by depositing droplets containing the relevant biological strands and leaving them the time to react with the surface of the intended sensing region 20.

In an embodiment, the surface of the sensing region 20 is modified using an appropriate surface layer, e.g. by forming a self-assembled monolayer (SAM) silanes, nanotubes or any other means that allow to anchoring of the receptors onto the surface of the sensing region 20, with the surface layer providing a handle for chemically (e.g. covalently) binding the biomolecule to the sensing surface. For instance, the biomolecules may be covalently linked to the SAM by reacting amine (e.g. $NH_2$) linkers of the respective biomolecules which can bind to suitable functional groups of the SAM.

Alternatively, the biomolecule may be directly anchored on a surface of a sensing region 20 that has been functionalized with appropriate handles. Such a handle may be a suitable functional group such as a thiol. This process is typically repeated until all sensing regions 20 are appropriately functionalized. It should be appreciated that it is not necessary for the functionalization process of a single sensing region 20 to be completed before the next sensing region can be functionalized; it is for instance equally feasible to deposit different droplets on all sensing regions 20, with the respective anchoring reactions taking place at the different sensing regions at least partially simultaneously.

Figure 3:
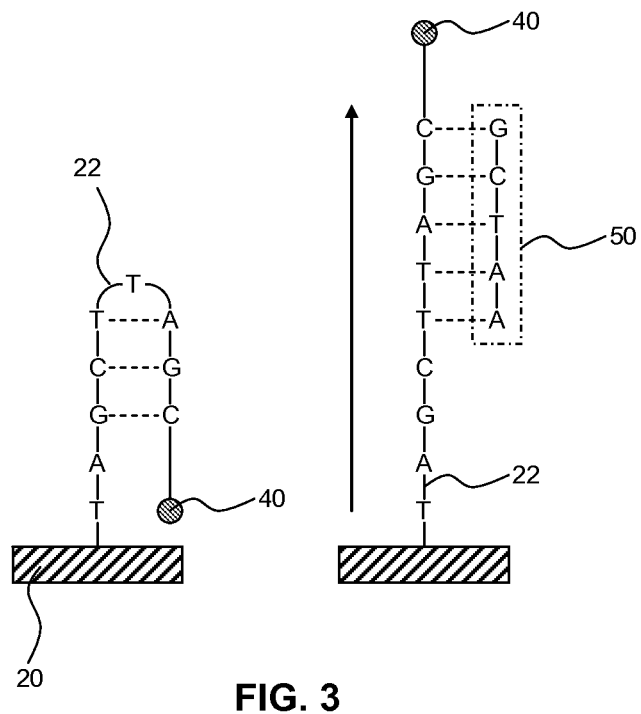
FIG. 3 schematically depicts a detection principle suitable for use with the present invention.

The detection principles underlying the present invention have already been described in great detail in the aforementioned prior art documents, and will therefore be briefly explained for the sake of brevity only with the aid of FIG. 3. In the left hand panel of FIG. 3, a sensing region 20 having anchored on its surface a biomolecule 22, here comprising a nucleotide sequence, is shown. In the absence of the analyte of interest, the biomolecule 22 may adopt a folded form, for instance because the largely lipophilic biomolecule is placed in a hydrophilic environment, e.g. an aqueous medium, such that the biomolecule 22 folds up to minimize its surface area exposed to the hydrophilic environment. Alternative driving forces may exist for the biomolecule 22 adopting a folded form. For instance, in case of the biomolecule 22 comprising a nucleotide sequence, as shown in FIG. 3, a hairpin may form due to the fact that the biomolecule comprises a palindrome that hybridizes with itself.

When the biomolecule 22 adopts a folded form, hairpin structure and so on, the mobility, e.g. Brownian motion, of the bead 40 and its attached biomolecule 22 is typically limited. Hence, in a dormant, i.e. unbound state, the different biomolecules generate a comparable time-varying sensor signal, as dictated by the limited motion caused by the curled up conformation adopted by the biomolecules.

However, when the biomolecule 22 engages in a specific binding event with its counterpart, i.e., the analyte of interest 50, as shown in FIG. 3, right hand panel by means of the hybridization event between part of the nucleotide sequence of the biomolecule 22 and the nucleotide sequence of the analyte of interest 50, the binding event forming the double-stranded DNA triggers the chain of the biomolecule 22 to extend, thus causing it to cover a much larger volume when moving around, e.g. as triggered by its Brownian motion. By using biomolecules having different chain lengths, e.g. biomolecules 22, 22' and 22", on a sensing region 20, the signature of the electrical/optical detection event and its evolution with time (e.g. variance) will tell whether binding to a long or to a short chain has happened, as the (tethered particle) volume occupied by the bead 40 over time will depend, i.e. is correlated to the chain length of the receptor biomolecule to which it is attached. This information can be translated into the binding of the analyte of interest 50 to its corresponding receptor, i.e. biomolecule immobilized or anchored on the surface of the sensing region 20.

It is reiterated that preferably the beads 40 should have the same specified dimension, as this ensures that the movement of the nanobeads 40 after binding of the analyte of interest 50 to the receptor biomolecule will heavily depend on the chain length of the receptor. The evolution of the electrical/optical signal associated to the binding will then also be indicative of the chain length of the probe biomolecule. It is however noted that different size beads 40 may also be used.

For instance, following the binding event in the example shown in FIG. 3, the nanobead 40, which may be connected either to the anchored receptor cDNA 22 or to the analyte DNA 50, will be connected to the surface of the sensing region 20 at an average distance proportional to the length of the anchored cDNA strand 22. The variation in electrical/optical signals in the readout of the sensing device will be indicative of the maximum excursion the bead/DNA system can still make. Hence, when multiple cDNA strands with substantially different chain lengths are anchored on the same sensing region 20, the user of the sensing device can distinguish between binding events occurring at strands with different chain lengths simply by analyzing the time-dependent variation of the sensor signal.

At this point, it is noted that the present invention is not limited to nucleotide chain-based receptor biomolecules such as DNA and RNA strands. Any suitable set of receptor molecules may be used. As will be clear from the aforementioned description of the present invention, a suitable set of receptor molecules may be defined as a set of receptor molecules comprising N*M receptor molecules having N sufficiently different lengths, e.g. chain lengths, when forming a binding pair with their specific analyte of interest. N and M are both positive integers, with N defining the degree of multiplexing that is achievable with the sensing device of the present invention and M is the number of sensing regions 20 of the sensing device.

Figure 4:
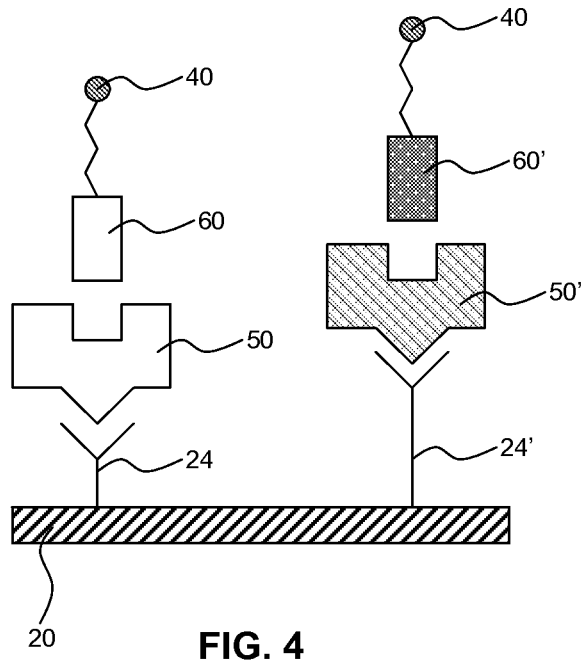
FIG. 4 schematically depicts another detection principle suitable for use with the present invention.

An alternative example of a sensing surface 20 comprising a plurality of suitable receptor biomolecules anchored at its surface is shown in FIG. 4. Here, two antibodies 24 and 24' are anchored at the surface of the sensing region 20 in any suitable manner. Anchoring of antibodies on a sensing surface is well-known per se and will not be explained further for reasons of brevity only.

Antibody 24 is arranged to form a specific binding pair with analyte of interest 50, which in turn may form another specific binding pair with a further antibody 60 comprising the label 40, e.g. a bead, fluorescent marker and so on. This principle may be recognized as an ELISA assay. Other assay types, e.g. competitive assays, are equally feasible. Antibody 24' forms an ELISA assay with further analyte of interest 50' and further antibody 60' to which another label 40 is attached. Due to the fact that the overall chain length of the assay formed by the antibody 24, analyte of interest 50 and the further antibody 60 is different to the chain length of the assay formed by the antibody 24', analyte of interest 50' and the further antibody 60', the labels 40 occupy a different excursion volume over time, which may be detected as previously described.

The different chain length may be achieved in any suitable way. For instance, the respective antibodies 24 and 24' may have different chain lengths, or may be anchored on the surface of the sensing device using respective spacer molecules (not shown) having a different chain length, as previously explained. Alternatively, the respective analytes of interest 50 and 50' may have different chain lengths, or the further antibodies 60 and 60' may have different chain lengths, in which case the antibodies 24 and 24' may have comparable chain lengths. In short, it is only required that the overall chain lengths of the respective binding pairs that can be formed on the surface of a single sensing region 20 are sufficiently different to facilitate the detection of individual binding events at the surface of the single sensing region 20.

It should be noted that the label 40, e.g. bead 40 may be attached to any of the components of the binding pair to be formed. For instance, the label may be attached to the receptor anchored on the surface of the sensing region 20, or may alternatively be attached to the analyte of interest 50. The label 40 may be indirectly attached to the analyte of interest 50, e.g. through a binding event between the analyte of interest 50 and an antibody such as the further antibody 60.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A sensing device comprising:
a substrate having a surface and having a plurality of individual sensing regions on said surface,
wherein each said sensing region includes a plurality of different length binding elements anchored on said surface for binding different specific analytes of interest, at least one of the specific analytes of interest and its matching binding element having a label for detecting said binding based on time-dependent variations in a signal caused by tethered particle motion.

2. The sensing device of claim 1, wherein each said binding element is unique and configured and arranged to exhibit different molecular dynamic behavior, and wherein the signal is radiated as an electrical or optical signal.

3. The sensing device of claim 1, wherein the binding elements on each said sensing region comprise different length biological molecules chemically bound on said surface.

4. The sensing device of claim 1, wherein the binding elements on each said sensing region comprise biological molecules anchored on said surface by different length spacer molecules.

5. The sensing device of claim 3, wherein the respective biological molecules comprise a nucleotide chain and wherein each of said binding elements has a nucleotide sequence complementary to the nucleotide sequence of one of the biological molecules such that the binding element is configured and arranged to bind the biological molecule.

6. The sensing device of claim 1, wherein the label comprises a bead, wherein each label is a similar size and is configured and arranged to scatter incident electromagnetic radiation.

7. The sensing device of claim 1, further comprising a detection circuit configured and arranged to detect binding of a specific analyte of interest to its matching binding element.

8. The sensing device of claim 7, wherein the sensing device includes an integrated circuit, said sensing regions being arranged on a surface of said integrated circuit, wherein the detection circuit forms part of the integrated circuit and includes a plurality of circuit elements respectively coupled to the sensing regions for electrically detecting the binding of a specific analyte of interest to its matching binding element and the detection circuit and plurality of circuit elements are further configured and arranged to distinguish between binding events occurring on the same sensing region based on the time-dependent variations in the signal caused by tethered particle motion.

9. The sensing device of claim 7, wherein the detection circuit comprises an optical element configured and arranged to optically detect the binding of a specific analyte of interest to its matching binding element and to distinguish between binding events occurring on the same sensing region based on the time-dependent variations in the signal caused by differences in tethered particle motion, wherein the differences in the tethered particle motion are correlated to an overall length of respective analytes of interest bound to their respective matching binding element.

10. An apparatus comprising the sensing device of claim 1, and an output circuit configured and arranged to provide a sensing result to a user of said apparatus.

11. A method of manufacturing a sensing device comprising a substrate having a surface and having a plurality of individual sensing regions on said surface, the method comprising, for each said sensing region, the steps of:
providing a droplet on said sensing region, said droplet having a plurality of different length binding elements for binding different specific analytes of interest; and
anchoring said different length binding elements on the surface of said sensing region wherein each binding element comprises a label for detecting the binding of the corresponding specific analyte of interest to said binding element based on time-dependent variations in a signal caused by tethered particle motion.

12. The method of claim 11, wherein the sensing device includes an integrated circuit, and wherein the label further for distinguishing between binding events occurring on the same sensing region based on the time-dependent variations in the signal caused by tethered particle motion.

13. The method of claim 11, wherein the binding elements on each sensing region comprise biological molecules having a different nucleotide chain length.

14. The method of claim 11, wherein said anchoring step comprises anchoring respective biological molecules on said surface using different length spacer molecules.

15. The method of claim 13, wherein the biological molecules and the plurality of different length binding elements each comprise a nucleotide sequence, the nucleotide sequence of each binding element being complementary to the nucleotide sequence of one of the specific biological molecules such that the binding element is configured and arranged to bind the specific biological molecule.

16. The method of claim 11, wherein said anchoring step comprises chemically binding said binding elements on the surface of said sensing region.

17. The sensing device of claim 8, wherein the detection circuit and the plurality of circuit elements are configured and arranged to detect a variation in the signal generated by the sensing region at which a binding event occurs.

18. The sensing device of claim 17, wherein the variation in the signal is correlated with the chain length of the specific biological molecule bound by the binding element.

19. The sensing device of claim 17, wherein the detection circuit and the plurality of circuit elements are configured and arranged to distinguish between binding events occurring on the same sensing region by analyzing the time-dependent variation in the signal.

20. The sensing device of claim 1, wherein the sensing device includes an integrated circuit having the surface, said sensing regions being arranged on the surface of said integrated circuit, and wherein the binding elements on each said sensing region comprise different length biological molecules chemically bound on said surface, the sensing device further comprising:

a detection circuit configured and arranged to detect binding of a specific analyte of interest to its matching binding element, wherein the detection circuit forms part of the integrated circuit and includes a plurality of circuit elements respectively coupled to the sensing regions and configured and arranged to electrically detect the binding of a specific analyte of interest to its matching binding element, and wherein the detection circuit and the plurality of circuit elements are configured and arranged to detect a variation in a signal generated by the sensing region at which a binding event occurs, and to distinguish between binding events occurring on the same sensing region by analyzing a time-dependent variation in the signal.

* * * * *